(12) United States Patent
Beverungen et al.

(10) Patent No.: US 8,293,315 B2
(45) Date of Patent: Oct. 23, 2012

(54) PROCESS FOR THE PREPARATION OF ACTIVE SUBSTANCE CONCENTRATE

(75) Inventors: Carsten Beverungen, Düsseldorf (DE); Albrecht Weiss, Langenfeld (DE); Eike Ulf Mahnke, Velbert (DE); Bernhard Gutsche, Hilden (DE)

(73) Assignee: Cognis IP Management GmbH, Duesseldorf (DE)

( * ) Notice: Subject to any disclaimer, the term of this patent is extended or adjusted under 35 U.S.C. 154(b) by 950 days.

(21) Appl. No.: 12/271,543

(22) Filed: Nov. 14, 2008

(65) Prior Publication Data

US 2010/0009063 A1 Jan. 14, 2010

(30) Foreign Application Priority Data

Nov. 17, 2007 (EP) .................................... 07022346

(51) Int. Cl.
*A23L 1/48* (2006.01)
(52) U.S. Cl. ........ 426/654; 426/655; 426/601; 426/602; 426/604
(58) Field of Classification Search .................. 426/654, 426/655, 601, 602, 604
See application file for complete search history.

(56) References Cited

U.S. PATENT DOCUMENTS 3,332,615 A * 7/1967 Aule ................................ 494/32
7,465,702 B2 * 12/2008 Reichlin et al. ............... 510/527

FOREIGN PATENT DOCUMENTS

WO    WO 98/46243    10/1998
WO    WO 2006/087119    8/2006

OTHER PUBLICATIONS

Foerster, Th. and Tesmann, H.: Phase Inversion Emulsification. In: Cosmetics & Toiletries. Dec. 1991, vol. 106, p. 49-52.
Foerster, Th., Von Rybinski, W., Tesmann, H. and Wadle, A: calculation of optimum emulsifier mixtures for phase inversion emulsification. In: International Journal of Cosmetic Science 16, 1994, p. 84-92.
Database WPI Week 199338, Thomson Scientific, London, GB; AN 1993-301490;XP002488993 & SU 1 763 475 A1.

* cited by examiner

*Primary Examiner* — Anthony Weier
(74) *Attorney, Agent, or Firm* — DiehlServilla LLC (57) ABSTRACT

Disclosed is a process for the preparation of active substance concentrates, which is distinguished in that an active-substance-containing starting material,
(i) (a) is either brought into contact with a PIT emulsion and the mixtures are heated to a temperature above the phase inversion temperature of the PIT emulsion, where they are held for a sufficient period of time, or
    (b) is brought into contact with an aqueous mixture of lipids and emulsifiers, which mixture is suitable for the formation of PIT emulsions, and the mixture is heated with strong shearing to a temperature above the phase inversion temperature with in-situ formation of a PIT emulsion, where the mixture is held for a sufficient period of time,
(ii) the mixtures are cooled and filtered and, if appropriate,
(iii) subjected to ultrafiltration and/or
(iv) a further solvent extraction.

16 Claims, 4 Drawing Sheets

PROCESS FOR THE PREPARATION OF ACTIVE SUBSTANCE CONCENTRATE

CROSS REFERENCE TO RELATED APPLICATIONS

This application claims the priority benefit of European Patent Application No. EP 07022346.6, filed Nov. 17, 2007 which is incorporated herein by reference in its entirety.

FIELD OF THE INVENTION

The invention concerns the field of botanical active substances and relates to the use of PIT emulsions as extractants.

BACKGROUND OF THE INVENTION

The trend of employing active substances which are not of synthetic, but of natural origin both for the production of cosmetic and pharmaceutical preparations and for food and feed additives has been observed for some time. The reasons for this are manifold: firstly, the mention of an active substance which has been taken directly from nature and has not been synthesized in a laboratory means that a consumer is prepared to pay higher prices; secondly, the processes for obtaining these active substances from predominantly botanical sources have been improved to such an extent that the active substance concentrates thus obtained can also be produced under economically useful conditions. Apart from that, many active substances are still easier to produce in a cell than in a bioreactor, even if a technical-scale synthetic route is known in the first place.

However, the term "natural raw material" is still understood as meaning a product which is obtained via the chemical route, in general by extraction, but where the product does not undergo any structural change during the process. Such extracts are usually prepared by aqueous, alcoholic or aqueous-alcoholic extraction of the plants or plant parts or of the leaves or fruits. In principle, all conventional extraction methods such as, for example, maceration, remaceration, digestion, dynamic maceration, fluidized-bed extraction, ultrasound-assisted extraction, countercurrent extraction, percolation, repercolation, evacolation (extraction under reduced pressure), diacolation or solid-liquid extraction with continuous reflux are suitable, percolation being the method of choice for technical-scale reactions. The starting material employed may be fresh plants or plant parts; however, one usually starts with dried plants and/or plant parts, which may be comminuted mechanically prior to the extraction. The solvent employed for carrying out the extractions may be organic solvents, water (preferably hot water with a temperature of above 80° C. and in particular of above 95° C.) or mixtures of organic solvents and water, in particular low-molecular-weight alcohols with more or less high water contents such as, for example, aqueous methanol, ethanol, pentane, hexane, heptane, acetone, propylene glycols, polyethylene glycols and ethyl acetate. As a rule, the extraction is carried out at from 20 to 100° C., preferably at from 30 to 90° C., in particular at from 60 to 80° C.

A disadvantage, however, is that the extractants must be adapted in each case to suit the polarity of the desired active substances, which means that the production of different active substances on different days in the same facility is complicated. Another unsatisfactory aspect is that only comparably small amounts may be extracted, within short periods, even when using solvents which are optimized for the respective active substance, or, vice versa, long extraction times are required for a higher extraction rate.

Accordingly, it was an object of the present invention to provide novel extractants with which the shortcomings of the prior art can be overcome and with the aid of which it is possible in particular to obtain higher extraction yields in shorter periods of time with less complex procedures and largely independently of the nature of the active substances to be extracted.

DETAILED DESCRIPTION OF PREFERRED EMBODIMENTS

The invention relates to a process for the preparation of active substance concentrates, which is characterized in that an active-substance-containing starting material
(i) (a) is either brought into contact with a PIT emulsion and the mixtures are heated to a temperature above the phase inversion temperature of the PIT emulsion, where they are held for a sufficient period of time, or
 (b) is brought into contact with an aqueous mixture of lipids and emulsifiers, which mixture is suitable for the formation of PIT emulsions, and the mixture is heated with strong shearing to a temperature above the phase inversion temperature with in-situ formation of a PIT emulsion, where the mixture is held for a sufficient period of time,
(ii) the mixtures are cooled and filtered and, if appropriate,
(iii) subjected to ultrafiltration and/or
(iv) a further solvent extraction.

Surprisingly, it has been found that the extraction of active-substance-containing starting materials, specifically botanical starting materials such as, for example, roots, leaves, peels, stems, pips, seeds and the like with the aid of PIT emulsions above the phase inversion temperature leads to markedly higher yields in shorter periods of time. The suitability of the PIT emulsions here is largely independent of the nature and in particular the polarity of the active substances to be extracted, which facilitates their use in industrial processes. A further advantage is that the PIT emulsions can be employed either directly as extractants or else their components—lipids, emulsifiers, water—are added separately to the starting materials, and the PIT emulsion is then prepared in-situ in the course of the extraction process.

Active Substances and Their Starting Materials

Without limiting the present invention thereto, the preferred active substances are active principles which are obtained from leaves, flowers, fruits, peels, stems, roots, seeds or pips of a very wide range of plants. Typical examples are extracts of the following plants: *Ginkgo biloba, Camellia sinensis, Olea europaea, Glyzyrrhiza glabra, Vaccinium myrtillus, Trifolium pratense, Litchi sinensis, Vitis vinifera, Brassica oleracea, Punica granatum, Petroselinum crispum, Centella asiatica, Passiflora incarnata, Melissa officinalis, Medicago sativa, Valeriana officinalis, Hoodia gordonii, Castanea sativa, Salix alba, Tagetes* and *Hapagophytum procumbens*. The text which follows will briefly describe the composition and the essential active substances in the extracts.

Ginkgo biloba

The active substances of the extracts which are obtained from the leaves of the ginkgo tree (*Ginkgo biloba*) are flavonoid glycosides which comprise, inter alia, (iso)quercitin glycosides, kaempferol, kaempferol-3 rhamnosides, isorhamnetin, luteolin glycosides, sitosterol glycosides and in particular hexacyclic terpene lactones, which are known as the ginkgolides A, B, C, J, M and bilobalides.

isorhamnetin ($R^1$ = H), kaempferol ($R^1$ = OH),
ginkgolide A ($R^1$ = OMe)

Camellia sinensis

Green tea leaves comprise a multiplicity of substances such as, for example, polysaccharides, volatile oils, vitamins, minerals, purines and, besides alkaloids such as caffeine, in particular polyphenols, which, as a rule, take the form of catechins and flavonoids and which are also referred to as "tea tannins".

| Components | R1 | R2 | R3 | R4 |
|---|---|---|---|---|
| (−)-Epicatechin | H | H | | |
| (−)-Epigallocatechin | H | OH | | |
| (−)-Epicatechin gallate | galloyl | H | | |
| (−)-Epigallocatechin gallate | galloyl | OH | | |
| Theaflavin | | | H | H |
| Theaflavin monogallate A | | | galloyl | H |
| Theaflavin monogallate B | | | H | galloyl |
| Theaflavin digallate | | | galloyl | galloyl |

Olea europaea

The main constituent of the leaves of the olive tree (*Olea europaea*) is the antioxidant oleuropein, which is also the most important source of hydroxytyrosol.

oleuropein

Glycyrrhiza glabra

Main constituent of the extract of licorice *Glycyrrhiza glabra* is glycyrrhetic acid.

glycyrrhetic acid

Vaccinium myrtillus

Extracts of bilberry (*Vaccinium myrtillus*) comprise a mixture of at least 15 different anthocyanosides, such as, for example, the following:

Usually, the extracts comprise from 20 to 25% by weight of anthocyanosides, from 5 to 10% by weight of tannins and small amounts of a variety of alkaloids such as, for example, myrtin and epimyrtin, phenolic acids and glycosides of quercitrin, isoquercitrin and hyperoside.

*Trifolium pratense*

The main constituents of the extracts from red clover (*Trifolium pratense*) are isoflavones such as, for example, daidzein, genestein, formononentin and biochanin A and their glucosides such as, for example, ononin or sissostrin:

| Isoflavone glucosides | $R_1$ | $R_2$ | $R_3$ | $R_4$ |
|---|---|---|---|---|
| Daizidin | H | H | glucose | H |
| Genistin | H | H | glucose | OH |
| Ononin | H | $CH_3$ | glucose | H |
| Sissostrin | H | $CH_3$ | glucose | OH |

*Litchi sinensis*

Extracts obtained from the peel of the lychee fruit (*Litchi sinensis*) are high in flavone derivatives such as, for example, 2-phenyl-4H-1-benzopyrans, flavans, flavan-3-ols (catechins, catechin oligomers), flavan-3,4-diols (leucoanthocyanides), flavones, flavonols and flavonones. The main constituent, however, is made up of condensed tannins, also known as procyanodols (OPCs). These substances comprise from 2 to 8 monomers of catechin or of a catechin species such as, for example, procyanidin, proanthocyanidin, procyanidole, oligoprocyanidin, leucoanthocyanidin, leucodelphinin, leucocyanin and anthocyanogen. OPCs, preferably proanthocyanidin A2 (OPC A2), behave like vitamin P, mainly with respect to the inhibition of matrix metal proteases.

oligomeric proanthocyanidin

*Vitis vinifera*

The main constituents from leaves, roots and in particular skins of grapes (*Vitis vinifera*) are polyphenols of the above-described OPC type.

The main constituents of the extracts from cauliflower (*Brassica oleracea*) are amino acids, in particular methionin and cysteine and the glucosinolates such as, for example, glucoraphanin.

*Punica granatum*

Pomegranate (*Punica granatum*) extracts comprise, besides sugars and citric acid, in particular delphinidine-1,2-glycosides and their aglycons.

*Petroselinum crispum*

The main constituent of the fatty oil of parsley (*Petroselinum crispum*) is petroselinic acid. The extracts, however, are high in apiol (1-allyl-2,5-dimethoxy-3,4-(methylenedioxy)benzene), and also apiin, myristicin, pinene and selinene.

apiol

*Centella asiatica*

Main constituents of the extracts from *Centella asiatica* are highly-condensed naphthenic acids, specifically asiatic acid, madecassic acid and their glycosides.

asiatic acid madecassic acid asiaticoside madecassoside

*Passiflora incarnata*

Extracts from passion fruit (*Passiflora incarnata*) are high in flavones of the apigenin and luteolin type and their C-glycosides apigenin luteolin

Furthermore, they comprise 2"-B-D-glucosides, schaftosides and isoschaftosides, isovitexin, isoorientin, vicenin-2, incenin-2, daponanin and trace elements, especially calcium, phosphorus and iron.

*Medicago sativa*

Extracts from alfalfa (*Medicago sativa*) are high in isoflavones such as, for example, daidzein, genestein, formononetin, biochanin A and tricin:

daidzein genestein formononetin biochanin A tricin

*Valeriana officinalis*

The main constituents of extracts from *Valeriana officinalis* are valeric acid, valerianone and borneol esters.

*Castanea sativa*

Extracts from sweet chestnut (*Castanea sativa*) comprise mainly saponins and also escin, which is the mixture of two glycosides whose aglycons are derived from proteoescigenin, while the sugars are either glucoronic acid or two molecules of D-glucose. The two glycosides differ by the nature of the acyl groups in the C22 position.

R - tiglinic acid or angelic acid

While α-escin is an amorphous powder which melts at 225 to 227° C. and is readily soluble in water, β-escin (also referred to as flogencyl) is present in the form of scales which are virtually insoluble in water, but readily soluble in alcohol.

*Hoodia gordonii*

Hoodia, specifically *Hoodia gordonii*, is a cactus plant which is indigenous to South Africa and has been known for a long time among the local population as a means for combating the sensation of hunger. It has been reported that, a long time ago, bushmen out hunting managed to survive for several weeks virtually without any food only by chewing hoodia roots. In recent years, it has been found that the amazing properties of this plant are the result of its high content of specific, active steroid glycosides. In 2001/2002, one of these species has for the first time been successfully isolated and characterized; it has since been referred to in the literature as substance P57:

(1)

To date, little is known from the patent literature about hoodia and hoodia extracts. The international patent application WO 98/046243 A1 (CSIR), however, discloses pharmaceutical preparations based on extracts of plants of the genus *Trichocaulon* or *Hoodia* which are said to have an appetite-suppressant effect.

*Salix alba*

Main constituents of the extracts from *Salix alba* are phenol glycosides and in particular salicylates such as, for example, salicin, salicortin and tremulacin:

salicin

*Tagetes*

The various species which belong to the genus *Tagetes* are high in carotenoids, in particular lutein and zeaxanthin.

*Harpagophytum procumbens*

The main constituents of the extracts from devil's claw (*Harpagophytum procumbens*) are iridoid glucoside, harpagoside, harpagide and procumbide.

iridoid glucoside
R = PhCH=CHCO— = harpagoside

R = H - harpagide

Stachylose and glycosylated phytosterols (for example β-sitosterol), flavonoids (for example kaempferol, luteolin), phenolic acids and glycosidic phenylpropanoic esters (for example verbacoside, isoacteoside) are furthermore found.

Other examples of suitable starting materials which can be subjected to extraction with PIT emulsions are peels of citrus fruit or pulverized and roasted coffee beans.

PIT Emulsions

An emulsion is understood as meaning a finely divided mixture of two different liquids (which are normally not miscible) without visible phase separation. Hydrophilic liquids form mainly intermolecular forces in the form of hydrogen bridges. In the case of lipophilic liquids, in contrast, it is mainly intramolecular Van-der-Waals forces which form. If a small amount of oil is placed in water, the oil will float. The smallest possible interface has formed between water and oil. The abovementioned forces cannot quite develop between the two phases. In contrast, an interfacial tension forms at the interface. The interfacial tension drives the formation of the smallest possible interface and thus prevents the existence of an emulsion. Therefore, specific substances which are active at the interface and which have emulsifying properties are required for preparing and stabilizing an emulsion. The interfacial tension at the oil/water phase interface is reduced considerably by the emulsifier, mixing only being made possible as a result of this. Despite this, emulsions are unstable systems, which means that their life is limited. What is known as "breaking of the emulsion" takes place as a result of the size of the interfaces being reduced by the droplets coalescing to form larger droplets. A PIT emulsion differs from other emulsions due to the fact that they form highly stable oil particles in the μm range and are capable of being diluted with water at suitable temperatures. It is highly characteristic that the oil:emulsifier ratio amounts to a multiple of the normal emulsions, as a rule, 10 to 20% by weight of emulsifier based on the lipid. The preparation of such systems is well known from the prior art; reference may be made as representation thereof to the publications by T. Förster et al. in Cosm. Toil. 106, 49-52 (1991) and Int. J. Cosm. Sci. 16, 84-92 (1994).

Lipids

Examples of lipids which are suitable for the preparation of the PIT emulsions are the following: Guerbet alcohols which are based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Others which are suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as, for example, propylene glycol, dimer diol or trimer triol) and/or Guerbet alcohols, triglycerides based on $C_6$-$C_{10}$-fatty acids, liquid mono/di/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol® CC), Guerbet carbonates based on fatty alcohols having 6 to 18, preferably 8 to 10, C atoms, esters of benzoic acid with linear and/or branched $C_6$-$C_{22}$-alcohols (for example Finsolv® TN), linear or branched, symmetric or asymmetric dialkyl ethers having 6 to 22 carbon atoms per alkyl group such as, for example, dicaprylyl ether (Cetiol® OE), ring-opening products of epoxidized fatty acid esters with polyols, silicone oils (cyclomethicone, silicon methicone types and the like) and/or aliphatic or naphthenic hydrocarbons such as, for example, squalane, squalene or dialkylcyclohexanes.

Emulsifiers

Emulsifiers which are suitable for the preparation of the PIT emulsions are, for example, nonionic surfactants from at least one of the following groups:

adducts of 2 to 30 moles of ethylene oxide and/or 0 to 5 moles of propylene oxide with linear fatty alcohols having 8 to 22 C atoms, with fatty acids having 12 to 22 C atoms, with alkylphenols having 8 to 15 C atoms in the alkyl group and alkylamines having 8 to 22 carbon atoms in the alkyl radical;

alkyl and/or alkenyl oligoglycosides having 8 to 22 carbon atoms in the alk(en)yl radical and their ethoxylated analogs;

adducts of 1 to 15 moles of ethylene oxide with castor oil and/or hydrogenated castor oil;

adducts of 15 to 60 moles of ethylene oxide with castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms and their adducts with 1 to 30 moles of ethylene oxide;

partial esters of polyglyerol (average degree of autocondensation 2 to 8), polyethylene glycol (molecular weight from 400 to 5000), trimethylolpropane, pentaerythritol, sugar alcohols (for example sorbitol), alkylglucosides (for example methyl glucoside, butyl glucoside, lauryl glucoside) and polyglucosides (for example cellulose) with saturated and/or unsaturated, linear or branched fatty acids having 12 to 22 carbon atoms and/or hydroxycarboxylic acids having 3 to 18 carbon atoms and their adducts with 1 to 30 moles of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol;

mono-, di- and trialkylphosphates and mono-, di- and/or tri-PEG-alkyl phosphates and their salts;

wool wax alcohols;

polysiloxane/polyalkyl/polyether copolymers and corresponding derivatives;

block copolymers, for example polyethylene glycol-30 dipolyhydroxystearates;

polymer emulsifiers, for example Pemulen types (TR-1, TR-2) from Goodrich or Cosmedia® SP from Cognis;

polyalkylene glycols and glycerol carbonate.

Alkoxylates. The adducts of ethylene oxide and/or of propylene oxide with fatty alcohols, fatty acids, alkylphenols or with castor oil are known, commercially available products. They are homolog mixtures whose mean degree of alkoxylation corresponds to the ratio of the amounts of ethylene oxide and/or propylene oxide and substrate with which the addition reaction is carried out. $C_{12/18}$-fatty acid mono- and diesters of adducts of ethylene oxide and glycerol are known as superfatting agents for cosmetic preparations.

Alkyl and/or alkenyl oligoglycosides. Alkyl and/or alkenyl oligoglycosides, their preparation and their use are known from the prior art. They are prepared in particular by reacting glucose or oligosaccharides with primary alcohols having 8 to 18 carbon atoms. As regards the glycoside residue, both monoglycosides, where a cyclic sugar residue is glycosidically bound to the fatty alcohol, and oligomeric glycosides with a degree of oligomerization of preferably approximately up to 8 are suitable. The degree of oligomerization here is a statistic mean which is based on a homolog distribution which is customary for such technical products.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and their technical mixtures which may still comprise small amounts of triglyceride in minor quantities as a result of the preparation process. Others which are suitable are adducts of from 1 to 30, preferably from 5 to 10 moles of ethylene oxide and the abovementioned partial glycerides.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and their technical mixtures. Others which are suitable are adducts of from 1 to 30, preferably from 5 to 10 moles of ethylene oxide and the abovementioned sorbitan esters.

Polyglycerol esters. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate and their mixtures. Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, which mono-, di- and triesters have optionally been reacted with from 1 to 30 moles of ethylene oxide.

Anionic emulsifiers. Typical anionic emulsifiers are aliphatic fatty acids having 12 to 22 carbon atoms such as, for example, palmitic acid, stearic acid or behenic acid, and dicarboxylic acids having 12 to 22 carbon atoms, such as, for example, azelaic acid or sebacic acid.

Amphoteric and cationic emulsifiers. Other emulsifiers which can be used are zwitterionic surfactants. The term "zwitterionic surfactants" refers to those surface-active compounds which have at least one quaternary ammonium group and at least one carboxylate and one sulfonate group in the molecule. Especially suitable zwitterionic surfactants are what are known as betaines such as the N-alkyl-N,N-dimethylammonium glycinates, for example cocoalkyldimethylammonium glycinate, N-acylaminopropyl-N,N-dimethylammonium glycinates, for example cocoacylaminopropyldimethyl-ammonium glycinate, and 2-alkyl-3-carboxylmethyl-3-hydroxyethylimidazolines with in each case 8 to 18 C atoms in the alkyl or acyl group, and cocoacylaminoethylhydroxyethyl carboxymethylglycinate. Especially preferred is the fatty acid amide derivative which is known by the CTFA name *Cocamidopropyl betaine*. Other emulsifiers which are suitable are ampholytic surfactants. Ampholytic surfactants are understood as meaning those surface-active compounds which, besides a $C_{8/18}$-alkyl or acyl group, have at least one free amino group and at least one —COOH or —SO$_3$H group in the molecule and which are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminoprop-ionic acids and alkylaminoacetic acids with in each case approximately 8 to 18 C atoms in the alkyl group. Especially preferred ampholytic surfactants are N-cocoalkyl aminopropionate, cocoacylaminoethyl aminopropionate and $C_{12/18}$-acylsarcosin. Finally, other emulsifiers which are suitable are cationic surfactants, with those of the esterquat type, preferably methyl-quaternized difatty acid triethanolamine ester salts, being especially preferred.

To prepare the PIT emulsions, the lipids and the emulsifiers are used as described further above, usually in amounts in the range of from 90:10 to 70:30 by weight and preferably around 80:20, and processed with 3 to 10-fold the amount of water in a manner known per se, i.e. while supplying a large amount of energy by stirring to the emulsion. The emulsions which can be obtained in this manner have a droplet diameter in the range from 0.01 to 0.5 µm and preferably from 0.03 to 0.3 µm, it being preferred that at least 50% of all droplets have a diameter of from 0.05 to 0.09 µm and in particular from 0.04 to 0.06 µm. The PIT emulsions can be prepared batchwise, as described in the prior art, but they are preferably prepared continuously since, in this manner, a narrower droplet size distribution is achieved. Naturally such products are useful firstly for further uses in technology, but they are also suitable, for example, for use in screening assays which are usually directed at aqueous test solutions.

Accordingly, a further subject matter of the present patent application relates to a process for the continuous preparation of PIT emulsions, in which a mixture of lipids and emulsifiers is homogenized, in a micromixer, with an aqueous phase, preferably in a weight ratio of from 90:10 to 70:30, and the preparation is heated by means of a microheat exchanger to a temperature above the phase inversion point and is then cooled using at least one further microheat exchanger. The use of PIT emulsions which have been prepared as described in the above continuous process using microreaction technology permits the extraction of more active substance as a result of the larger total surface area of the droplets. At the same time, the emulsions also have better stability, and require little space when storing the starting materials and end products. Here, the invention takes into consideration the fact that, when swapping the microreactors for conventional reactors, PIT emulsions are obtained which have droplet size distributions as are also known from the batch method.

Procedure of the Extraction Process

In a first embodiment of the present invention, the PIT emulsion is first prepared by one of the above-described processes, using an oil and a water phase, it being preferred to use the continuous microreaction preparation process. As a rule, the active-substance-containing materials are suspended in the PIT emulsions and heated with warming to above the respective phase inversion temperature. If this temperature is not known, the formation of the PIT emulsion can be monitored via the conductivity: with increasing temperature, the conductivity drops continuously as the amount of aqueous continuous phase decreases, and reaches the value zero above the PIT. When reaching or exceeding the PIT, the extraction is carried out over a sufficient period of time, which may differ greatly between cases, but is, in general, at least one hour and rarely more than 4 hours. Thereafter, the mixtures are cooled again, and the insoluble constituents are filtered off. The active substance concentrates thus obtained may already constitute end products which are ready for sale; in many cases, however, a further purification and concentration is recommended. This includes in particular a re-separation of the PIT emulsion into an aqueous and an oil-containing phase, which is achieved for example by breaking the emulsions by means of ultrafiltration or membrane filtration. It can be detected analytically that—depending on the active substance—the vast majority, i.e. more than 80 and in particular more than 90% of the—generally lipophilic—active substances can be found in the organic phase. The organic phase as such may now also be used as a commodity, for example for the cosmetics industry. However, it is also possible to employ a further solvent extraction and to concentrate the active substances in a polar organic phase, from which they are then obtained in solid form by crystallization, spray-drying or freeze-drying.

As an alternative, the extraction may also be carried out with in-situ formation of the PIT emulsions. Instead of the readily provided PIT emulsions, for this procedure their individual components are employed, and heated together with the active-substance-containing starting materials to above the phase inversion temperature. This is preferably carried out while supplying energy by stirring in order to generate as small droplets as possible.

The advantage of this procedure is that even moist material can be exploited for the extraction, that the extraction components can be selected depending on operational requirements (for example avoiding explosionproofness), that the selectivity can be controlled by selecting the surfactant/oil mixture, and that the way in which the process is conducted makes it possible to set an interfacial tension which is indeed as low as possible.

Industrial Applicability

A further subject matter of the present patent application is the use of PIT emulsions as extractants for active-substance-containing starting materials, in particular botanical materials, specifically their leaves, flowers, fruits, peels, stems, roots, seeds or pips.

EXAMPLES

Example 1

Batchwise Preparation of a PIT Emulsion

Figure 1:
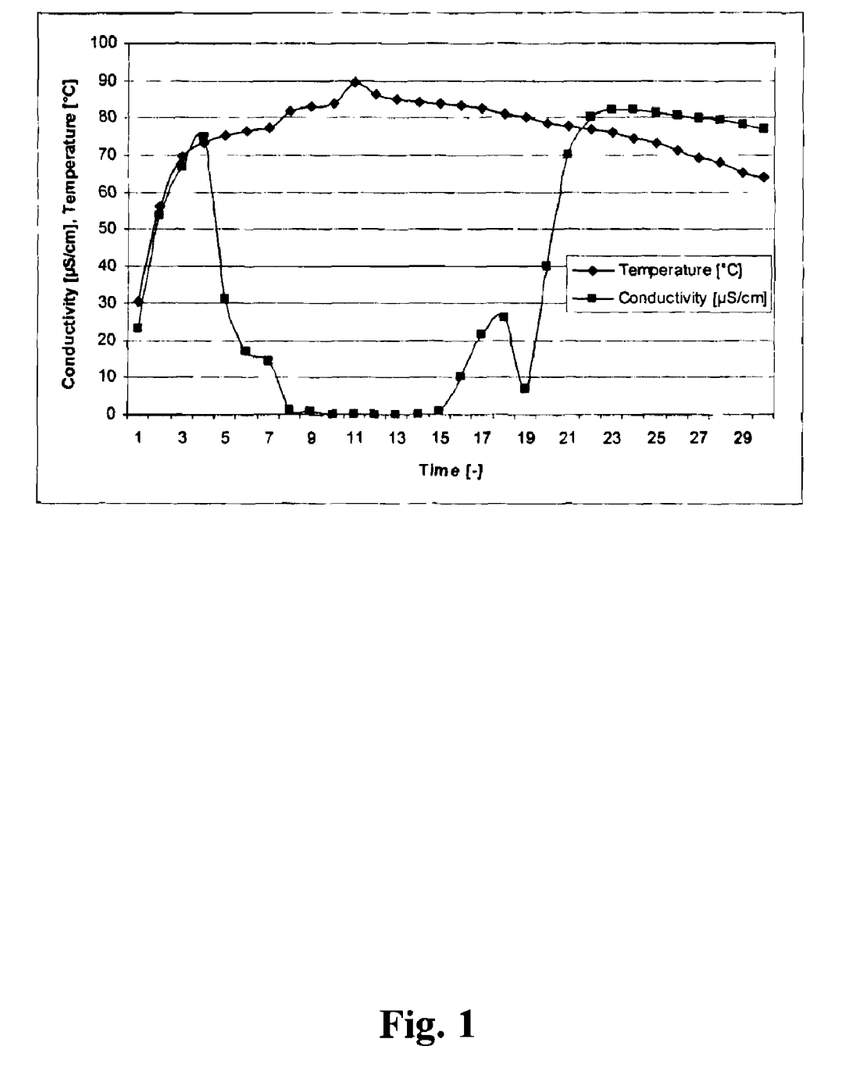
FIG. 1 is a temperature/conductivity diagram of the PIT emulsion as prepared in the batchwise process of Example 1.

In a 250 ml flask, 3.1 g of glycerol stearate (Cutina® GMS), 6.9 g of ceteareth-12 (Eumulgin® B1), 22.5 g of dicaprylyl ether (Cetiol® OE), 22.5 g of dioctyl cyclohexane (Cetiol® S), 5 g of glycerol and 40 ml of water were mixed with one another with vigorous stirring and warmed from 25° C. to 95° C. within 140 min. Thereafter, the mixture was cooled back down to the starting temperature within 20 min. In order to monitor the formation of the PIT emulsion, the conductivity was monitored as a function of time. The curve shape is shown in FIG. 1.

Figure 2:
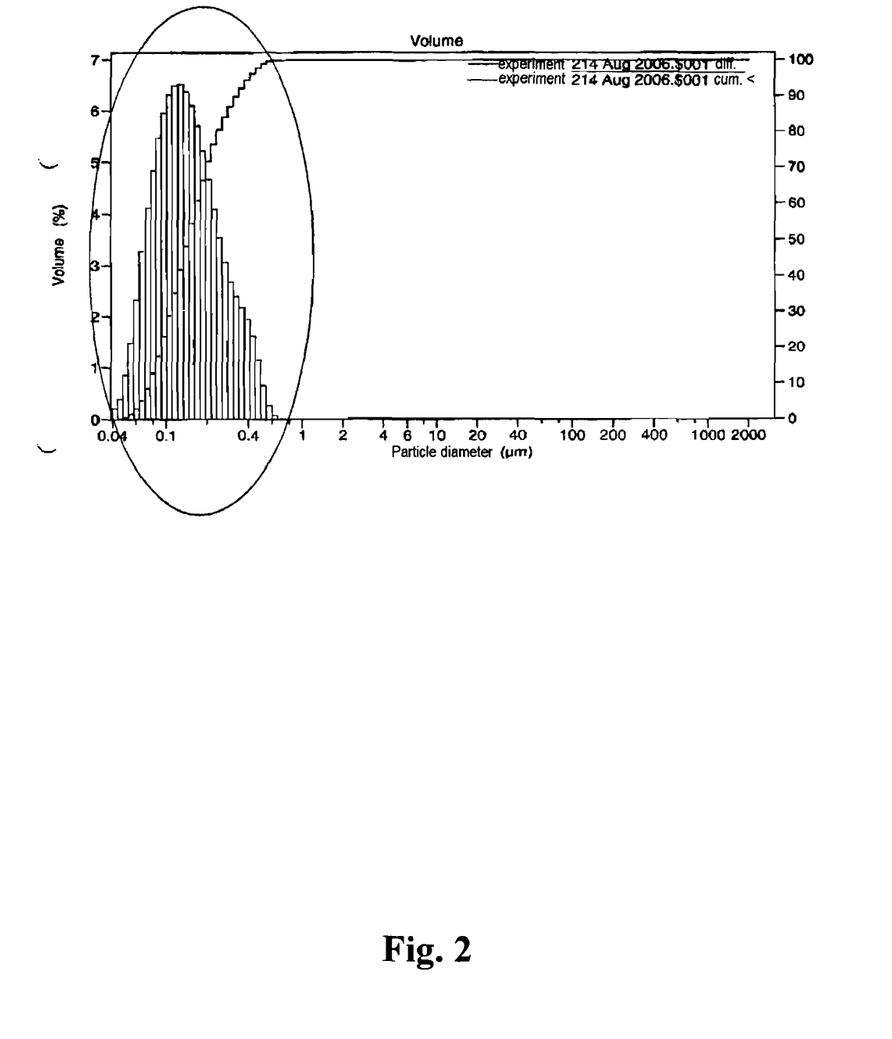
FIG. 2 is a graph of the particle size distribution of the PIT emulsion as prepared in the batchwise process of Example 1.

The conductivity drops with increasing temperature and reaches the value zero around the PIT temperature; then, the conductivity increases again with decreasing temperature. This can be explained by the fact that an O/W emulsion where the water is the continuous phase is present below the PIT temperature; above the PIT temperature, the oil then forms the continuous phase, which leads to the loss of the conductivity. Thus, the curve shape clearly indicates the formation of a PIT emulsion. The mixture thus obtained showed the properties for which PIT emulsions are known, which are high stability, miscibility with water in any ratio, very small droplet sizes and a bluish tinge. In addition, samples were taken, and their droplet size was determined using a Coulter LS particle size analyzer (FIG. 2)

Example 2

Continuous Preparation of a PIT Emulsion

Figure 3:
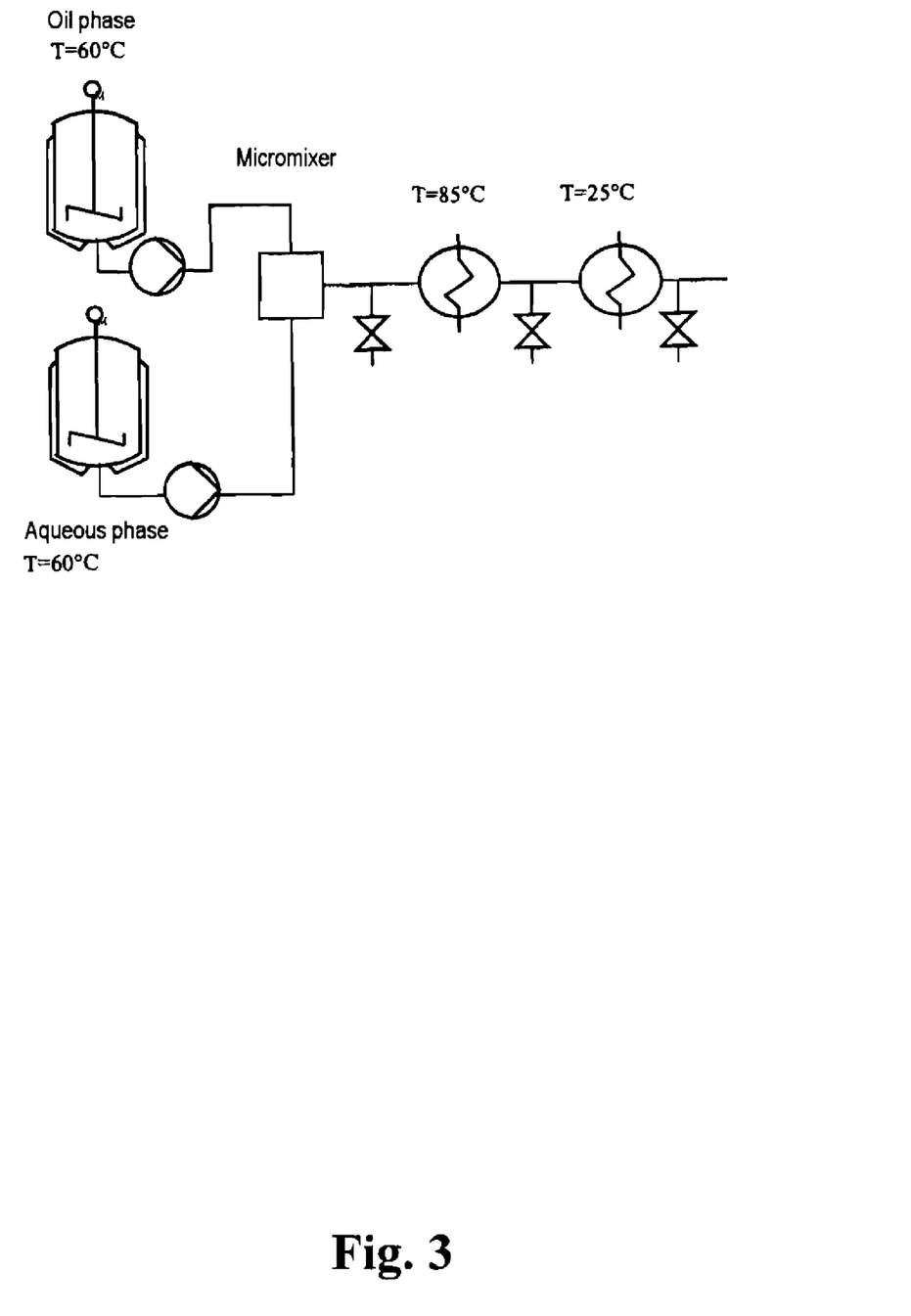
FIG. 3 is a flow diagram for the continuous preparation of PIT emulsions as prepared in Example 2.

For rapidly increasing and then rapidly lowering the temperature in the continuous preparation of the PIT emulsion, a micromixer of the StarLaminator 30 type, IMM, was connected with two microheat exchangers. The receiving vessels used for the aqueous phase and the oil phase were two 15 l double-walled glass reactors; the flow diagram is shown in FIG. 3.

The oil phase consisting of 1.24 kg of Cutina® GMS, 2.76 kg of Eumulgin® B1, 9.00 kg of Cetiol® OE and 9.00 kg of Cetiol® S and the aqueous phase consisting of 2 kg of glycerol dissolved in 16 kg of distilled water were initially introduced separately in a storage container and prewarmed to T=60° C. During this process, both phases were stirred. The two phases (oil phase:aqueous phase 1.22:1) were pumped into the micromixer as two different volumes streams (6 l/h and 12 l/h) and mixed in the micromixer. Directly after the StarLam 30 mixer, the mixture was heated in a microheat exchanger to 85° C., so that the phase inversion temperature (81° C.) was exceeded. Thereafter, the emulsion was cooled in a second microheat exchanger to a temperature of T=25° C. and collected in a storage container. In each case, after the micromixer and after the two heat exchangers, a sample was taken and its temperature and conductivity was determined. Before the first heat exchanger, the conductivity was approximately 55 μS/cm, after the first microheat exchanger it dropped to a value of 0.1 μS/cm and, after the emulsion had cooled, it climbed to approx. 60 μS/cm. In this manner, the formation of true PIT emulsions was detected.

Figure 4:
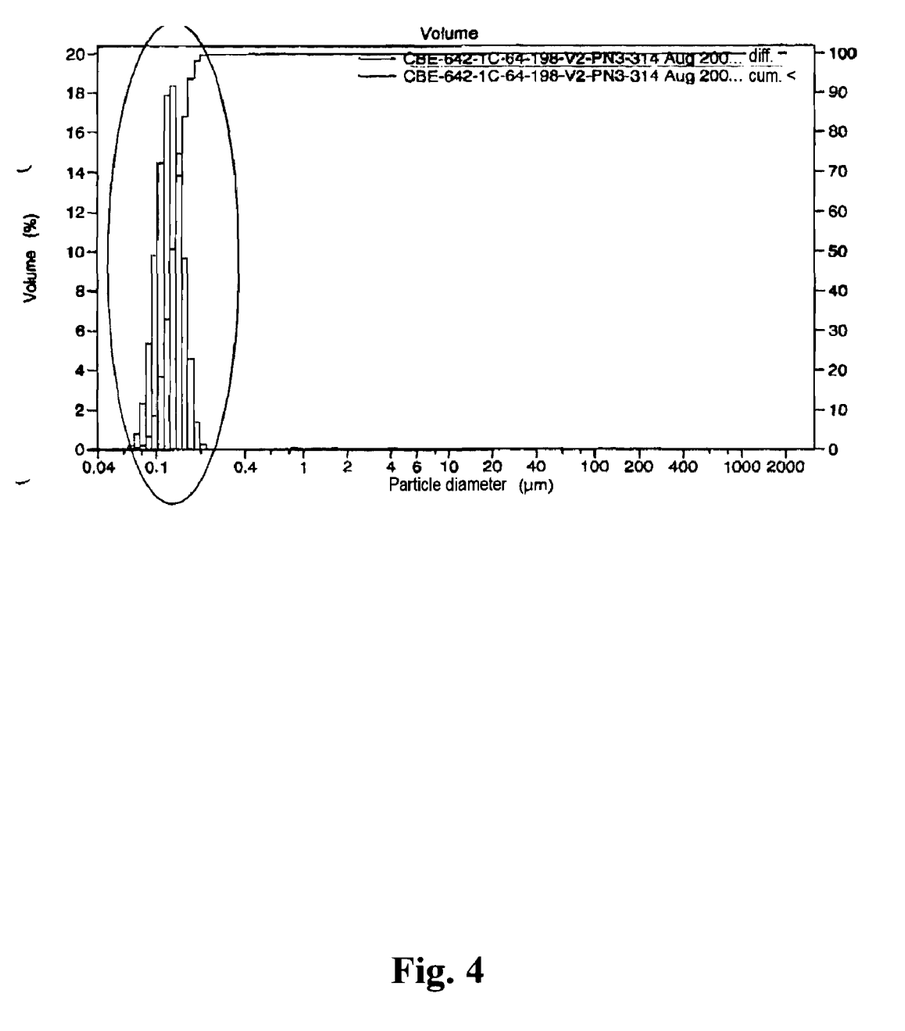
FIG. 4 is a graph of the particle size distribution of the PIT emulsion as prepared in the continuous process of Example 2.

In addition, samples were taken, and their droplet size was determined with a Coulter LS particle size analyzer (FIG. 4).

The particle sizes measured are approx. 0.125 μm and therefore smaller than the particle sizes obtained by the batch method (approx. 0.165 μm).

Example 3

Extraction of Botanical Material with PIT Emulsions

A variety of botanical starting materials (olive leaves, orange peel, coffee powder) was comminuted and added to an emulsion prepared as described in Examples 1 and 2. Thereafter, the preparations were heated with stirring over 4 hours to a temperature of approx. 90° C., i.e. close to the phase inversion temperature. After cooling, the mixtures were first filtered in order to remove insoluble residues and then subjected to ultrafiltration in order to generate an aqueous and an oil-containing phase. The content of botanical active substances in the two phases was determined by extraction with acetonitrile followed by HPLC analysis. The results are compiled in Table 1:

TABLE 1

Extraction of aqueous phase and oil phase

| Starting material | Aqueous phase [mg] | Oil phase [mg] | Total [mg] | Percentage of active substances in the oil phase [%] |
| --- | --- | --- | --- | --- |
| Olive leaves | 60.0 | 340.0 | 400.0 | 85 |
| Orange peel | 46.0 | 114.0 | 160.0 | 91 |
| Coffee powder | 2.4 | 91.6 | 94.0 | 97 |

In this manner, it was possible to demonstrate that the botanical active substances were predominantly, i.e. in amounts of between 85 and 97%, concentrated in the oil phase.

Example 4

Comparison of PIT Emulsions with Other Extractants 1 kg of olive leaves were treated in each case with 2 l of different extractants for 4 hours at 90° C., and the oleuropein content was subsequently determined via HPLC; the highest content was set at 100% and all the other results were related thereto. The results are compiled in table 2:

TABLE 2

Extraction of oleuropein

| Extractant | Oleuropein content |
| --- | --- |
| PIT emulsion according to Example 2 | 100 |
| Ethanol | 74.3 |
| Acetonitrile | 42.0 |
| Ethyl methyl ketone | 40.7 |
| Dicaprylyl ether | 0 |

The results show clearly that approximately 25% more active substances are extracted when PIT emulsions are used than, for example, with the standard extractant ethanol.

Example 5

In-situ Extraction of Zeaxanthin and Lutein 2 kg of an oil phase according to Example 2 were mixed for t=30 min with 750 g of Tagetes petals at $T_1$=50° C. Thereafter, 5 l of distilled water were added, and the mixture was heated to $T_2$=95° C. ($\Delta T$=0.5° C./min). After cooling, the mixtures were first filtered in order to remove insoluble residues and then subjected to ultrafiltration in order to generate an aqueous and an oil-containing phase. The zeaxanthin and lutein contents—based on the total amount—were 92% in the oil phase and 8% in the aqueous phase.

We claim:

1. A process for the preparation of a botanical active substance concentrate, comprising
    (a) contacting a botanical active-substance-containing starting material with a PIT emulsion to form a mixture,
    (b) heating said mixture to temperatures above the phase inversion temperature of the PIT emulsion, for a sufficient period of time,
    (c) cooling and filtering said mixture to form the concentrate,
    (d) optionally subjecting said concentrate to ultrafiltration, and
    (e) optionally further extracting said concentrate,
    wherein the botanical active-substance-containing starting material is selected from the group consisting of leaves, flowers, fruits, peels, stems, roots, seeds, pips of plants and mixtures thereof.

2. A process for the preparation of a botanical active substance concentrate, comprising
    (a) contacting a botanical active-substance-containing starting material with an aqueous mixture of lipids and emulsifiers which is suitable for forming PIT emulsions, to form a mixture,
    (b) heating said mixture with strong shearing to temperatures above the phase inversion temperature with in-situ formation of a PIT emulsion, for a sufficient period of time,
    (c) cooling and filtering said PIT emulsion to form the concentrate,
    (d) optionally subjecting said concentrate to ultrafiltration, and
    (e) optionally further extracting said concentrate,
    wherein the botanical active-substance containing starting material is selected from the group consisting of leaves, flowers, fruits, peels, stems, roots, seeds, pips of plants and mixtures thereof.

3. The process of claim 1, wherein said botanical active-substance-containing starting material is selected from the group consisting of leaves, flowers, fruits, peels, stems, roots, seeds, pips of plants and mixtures thereof, wherein said plants are selected from the group formed by consisting of *Ginkgo biloba, Camellia sinensis, Olea europaea, Glyzyrrhiza glabra, Vaccinium myrtillus, Trifolium pratense, Litchi sinensis, Vitis vinifera, Brassica oleracea, Punica granatum, Petroselinum crispum, Centella asiatica, Passiflora incarnata, Melissa officinalis, Medicago sativa, Valeriana officinalis, Hoodia gordonii, Castanea sativa, Salix alba, Tagetes* and *Hapagophytum procumbens*.

4. The process of claim 1, wherein said botanical active-substance-containing starting material is selected from the group consisting of peels of citrus fruit and coffee powder.

5. The process of claim 1, wherein said PIT emulsion comprises lipids and emulsifiers in a weight ratio of from about 90:10 to about 70:30.

6. The process of claim 1, wherein said PIT emulsion has a droplet size distribution in the range of from about 0.01 to about 0.5 µm.

7. The process of claim 1, wherein said PIT emulsion has a droplet size distribution wherein at least 50% of all droplets have a diameter in the range of from about 0.05 to about 0.09 µm.

8. A method of extraction comprising contacting botanical active-substance-containing starting materials with PIT emulsions and separating the resulting botanical active-substance-containing extract, wherein said botanical active-substance-containing starting materials are selected from the group consisting of leaves, flowers, fruits, peels, stems, roots, seeds, pips of plants, and mixtures thereof.

9. The process of claim 2, wherein said botanical active-substance-containing starting material is selected from the group consisting of peels of citrus fruit and coffee powder.

10. The process of claim 2, wherein said PIT emulsion comprises lipids and emulsifiers in a weight ratio of from about 90:10 to about 70:30.

11. The process of claim 2, wherein said PIT emulsion has a droplet size distribution in the range of from about 0.01 to about 0.5 µm.

12. The process of claim 2, wherein said PIT emulsion has a droplet size distribution wherein at least 50% of all droplets have a diameter in the range of from about 0.05 to about 0.09 µm.

13. The process of claim 8, wherein the botanical active-substance-containing starting materials are selected from the group consisting of peels of citrus fruit and coffee powder.

14. The process of claim 8, wherein said PIT emulsion comprises lipids and emulsifiers in a weight ratio of from about 90:10 to about 70:30.

15. The process of claim 8, wherein said PIT emulsion has a droplet size distribution in the range of from about 0.01 to about 0.5 µm.

16. The process of claim 8, wherein said PIT emulsion has a droplet size distribution wherein at least 50% of all droplets have a diameter in the range of from about 0.05 to about 0.09 µm.

\* \* \* \* \*